US012690825B2

(12) United States Patent
Ahnen et al.

(10) Patent No.: US 12,690,825 B2
(45) Date of Patent: Jul. 28, 2026

(54) METHOD TO POSITION A SUBJECT TO BE SCANNED IN A PET-SCANNING DEVICE

(71) Applicant: Positrigo AG, Zürich (CH)

(72) Inventors: Max Ludwig Ahnen, Zürich (CH); Jannis Nikolaus Rudolf Fischer, Zürich (CH); Ekaterina Mikhaylova, Riniken (CH)

(73) Assignee: Positrigo AG, Zurich (CH)

( * ) Notice: Subject to any disclaimer, the term of this patent is extended or adjusted under 35 U.S.C. 154(b) by 192 days.

(21) Appl. No.: 18/706,200

(22) PCT Filed: Oct. 25, 2022

(86) PCT No.: PCT/EP2022/079710
§ 371 (c)(1),
(2) Date: Apr. 30, 2024

(87) PCT Pub. No.: WO2023/078727
PCT Pub. Date: May 11, 2023

(65) Prior Publication Data
US 2025/0009315 A1      Jan. 9, 2025

(30) Foreign Application Priority Data
Nov. 4, 2021     (EP) ..................................... 21206526

(51) Int. Cl.
*A61B 6/04* (2006.01)
*A61B 6/00* (2006.01)
(Continued)

(52) U.S. Cl.
CPC ............ *A61B 6/0487* (2020.08); *A61B 6/037* (2013.01); *A61B 6/04* (2013.01); *A61B 6/0478* (2013.01);
(Continued)

(58) Field of Classification Search
CPC ......... A61B 6/037; A61B 6/04; A61B 6/0478; A61B 6/0487; A61B 6/461; A61B 6/488; A61B 6/501; A61B 6/54
See application file for complete search history.

(56) References Cited

U.S. PATENT DOCUMENTS 8,076,644 B2    12/2011  Wollenweber
2018/0317873 A1  11/2018  Xu
2021/0196219 A1   7/2021  Jansen et al.

FOREIGN PATENT DOCUMENTS

JP        2012-173237 A     9/2012
WO        2010/048309 A2    4/2010

OTHER PUBLICATIONS

Frederic H. Fahey, "Data Acquisition in PET Imaging", Journal of Nuclear Medicine Technology, vol. 30, No. 2, 2002, pp. 39-49.
(Continued)

*Primary Examiner* — Mark R Gaworecki
(74) *Attorney, Agent, or Firm* — Sughrue Mion, PLLC

(57)                    ABSTRACT
A method to position a subject to be scanned in a positron emission tomography (PET)-scanning device (1) is presented. According to this method, the subject to be scanned (P) is prepositioned in the PET-scanning device (1) and a set of PET-raw data is acquired of the subject to be scanned (P) for a series of slices by means of a detector (11) of the PET-scanning device (1). The acquired set of PET-raw data is represented in the form of at least one projection view, and the position of the subject to be scanned (P) relative to the detector (11) is directly assessed based on this at least one projection view. Furthermore, a PET-scanning device (1) configured to carry out this method and a computer program for controlling such a PET-scanning device are provided.

20 Claims, 6 Drawing Sheets

(51) Int. Cl.
     *A61B 6/03*         (2006.01)
     *A61B 6/46*         (2024.01)
     *A61B 6/50*         (2024.01)

(52) U.S. Cl.
     CPC .............. *A61B 6/461* (2013.01); *A61B 6/501*
          (2013.01); *A61B 6/54* (2013.01); *A61B 6/488*
                                  (2013.01)

(56)               References Cited

OTHER PUBLICATIONS

International Search Report for PCT/EP2022/079710 dated Feb. 10, 2023.
Written Opinion for PCT/EP2022/079710 dated Feb. 10, 2023.

Angle

Image per Slice

Slice

Image per Angle / Angle Range

LOR

11

111

P

METHOD TO POSITION A SUBJECT TO BE SCANNED IN A PET-SCANNING DEVICE

CROSS REFERENCE TO RELATED APPLICATIONS

This application is a National Stage of International Application No. PCT/EP2022/079710 filed Oct. 25, 2022, claiming priority based on European Patent Application Ser. No. 21/206,526.2 filed Nov. 4, 2021.

TECHNICAL FIELD

The present invention relates to a method to position a subject to be scanned, in particular a human or animal patient, in a positron emission tomography (PET)-scanning device. The invention also relates to a PET-scanning device configured to carry out this method and to a computer program for controlling such a PET-scanning device.

PRIOR ART

In positron emission tomography (PET)-imaging, a considerable amount of time is often used for correctly positioning the patient with respect to the detector. A correct positioning of the patient is essential for achieving an optimal image quality. Only if the body part to be scanned is positioned centrally and with the right orientation within the detector of the PET-scanner, it is possible to acquire clinically useful images of high quality. Furthermore, the patient must remain as still as possible during the entire image acquisition period, in order to not cause any motion artefacts in the scanned images. In order to reduce movements of the patients in the scanner, the patient should also adopt as comfortable a position as possible in the scanner. Thus, for the outcome of the final PET-images, it is therefore crucial to position the patient in a way that is both optimal with respect to the PET-detector and comfortable for the patient. On the other hand, however, the positioning of the patient in the PET-scanning device should also take as little time as possible in view of the ongoing spread of the radioactive tracer in the patient's body and further in view of the usually high costs of the device making scan time expensive.

In prior art PET-scanning devices, the body part of the patient to be scanned is usually positioned relative to the detector with the help of visual laser markers that are projected on the patient. For example, in PET-scanning of the brain, a line laser is often used, in order to position and orient a detector ring of the PET-scanning device in relation to the patient's canthomeatal line.

Such visual positioning methods have the drawback that e.g. the exact positioning and orientation of the inner organ or body part which is of actual interest is not taken into account. For example, the position and orientation of the brain with respect to the skull and/or to the outer organs or features can vary from patient to patient. Also, when imaging a tumour, it might not be known during the positioning of the patient, where exactly the tumour is located within the patient's brain. Is far too time-consuming, however, to acquire a complete dataset of PET-imaging data and to reconstruct tomographic images, in order to assess and, if necessary, re-adjust the patient's position in relation to the detector.

U.S. Pat. No. 8,076,644 B2 discloses a method for aligning the patient's head with respect to the detector ring of a brain PET-scanning device. For this purpose, a count-rate profile of the brain is acquired which reflects the number of detected emission events within each of a plurality of axial slices. The detector is then repositioned in relation to the brain based on this count-rate profile and a detector sensitivity profile.

US 2021/0196219 A1 discloses a method to create a series of reconstructed tomographic PET-images of the head, in order to detect patient motion. By means of edge detection, patient motion is detected and measured, in order to correct the PET-images and avoid artefacts.

WO 2010/048309 A2 relates to a method for tracking and displaying interventional devices in PET-mammography imaging. In order to obtain the images in less time, the data processing is limited to a focal plane.

Besides, in the journal paper of Frederic H. Fahey, "Data Acquisition in PET Imaging", Journal of Nuclear Medicine Technology June 2002, 30 (2) 39-49, data acquisition as well as various methods for data storing in PET imaging are described. The paper, however, does not relate to patient positioning or motion in the PET-scanning device.

SUMMARY OF THE INVENTION

It is an object of the present invention to provide a fast and reliable method to position a subject to be scanned in a positron emission tomography (PET)-scanning device.

In order to achieve this object, the present invention provides a method to position a subject to be scanned in a positron emission tomography (PET)-scanning device, comprising the steps of:
- a) prepositioning the subject to be scanned in the PET-scanning device;
- b) acquiring, by means of a detector of the PET-scanning device, a set of PET-raw data of the subject to be scanned for a series of slices;
- c) representing the acquired set of PET-raw data in the form of at least one projection view; and
- d) assessing the position of the subject to be scanned relative to the detector directly based on the at least one projection view.

By using directly a representation of the PET-raw data, i.e. the at least one projection view, to assess the position of the subject to be scanned relative to the detector, no time- and computer-intensive tomographic reconstruction needs to be carried out. In this way, it is possible to assess the position of the patient's inner body parts relative to the detector in a fast and reliable way. The assessment of the position of the subject to be scanned can thus be made in step d) directly with respect to the organ or body part that is of actual interest with regard to the PET-imaging e.g. the patient's brain. Since usually during the positioning, the radioactive tracer is in the patient's body anyway, PET-raw data can already be acquired and be used for e.g. positioning purposes without exposing the patient to any additional radiation.

It is important to note, that the at least one projection view is not a reconstructed tomographic image, but a representation of the acquired set of PET-raw data. The at least one projection view can for example form a subset of the PET-raw data. Alternatively, the at least one projection view can be formed by means of reordering the PET-raw data and/or by means of simple calculations applied to the PET-raw data. For example, the acquired PET-raw data can be reordered such that a projection view from a certain viewing angle is obtained and/or computationally simple image filters and/or computationally simple image post-processing methods can be applied, such as e.g. brightness and contrast adjustments, binning, noise suppression or similar methods. In contrast to tomographic images, a projection view represents PET-raw data which are not limited to a certain thin slice, but instead represents PET-raw data of a larger volume, usually including entire organs of the subject to be scanned, such as e.g. a brain. Thus, in a projection view, different parts of one or more than one organ, different types of tissues and/or even different organs are usually displayed superimposed. For the purpose of assessing the position of the subject to be scanned, the projection view is sufficient in most cases.

In PET-imaging, the term "raw data" is well known to the person skilled in the art. The skilled person particularly distinguishes between the term "raw data" on the one hand and terms relating to reconstructed data, such as e.g. "reconstructed tomographic data" or "reconstructed images" on the other hand.

Raw data, as it is understood in the context of this document, are for example the primary data received from the detector of the PET-scanning device. Raw data particularly have not been subjected to any sophisticated processing. They might have been e.g. subjected to a standard efficiency correction and/or to a geometric normalization correction, but not to e.g. a forward and back projection method, in order to yield tomographic images. Raw data have particularly not been subjected to any processing methods that are dependent on user-inputs.

A reconstructed tomographic image is an image that is generated from the acquired raw data by means of an image reconstruction technique. The reconstructed tomographic image, which can also be referred to as a tomogram, reflects a slice or section through the scanned part of the subject. In PET-imaging, for obtaining a tomographic image from the raw data, a forward and back projection method is typically applied, which is usually highly computationally intensive. By contrast, with the proposed method, the PET-raw data are represented in the form of at least one projection view in step c). Thus, the at least one projection view which is used for assessing the position forms a representation of the PET-raw data, which does not need any tomographic reconstruction. The presented method for positioning a subject to be scanned in a PET-scanning device can be used in combination with multi-dimensional PET, including, but not limited to two-dimensional (2D)-PET or three-dimensional (3D)-PET. 3D-PET differs from 2D-PET in particular by the requirement of a 3D reconstruction technique, which usually is substantially more complicated and time consuming than 2D methods.

With the indication that the set of PET-raw data are acquired for a series of slices, it is meant that, the PET-raw data are acquired along at least one dimension, typically along at least two dimensions and preferably along at least three or more dimensions. Thus, the PET-raw data preferably relate to a three-dimensionally extending volume of the subject to be scanned. The slices are preferably arranged parallel and directly adjacent to each other. They can be, but do not need to be, oriented perpendicular to the main longitudinal axis of the detector. If the detector has the shape of a hollow cylinder, the main longitudinal axis is the geometrically defined cylinder axis.

The acquisition of the set of PET-raw data in step b) usually involves a detection of emissions from a radioactive tracer that is present within the body of the subject to be scanned. For this purpose, the detector, which preferably forms a ring-like or a polygon-like shape, usually comprises a plurality of sensors, in particular a plurality of sensor modules. The sensors can be arranged in a circumferential or a polygonal ring, in order to be positioned around e.g. a patient's head for detecting PET-radiation emitted from the patient's head. The detector ring can particularly form a closed ring, i.e. it can be closed in the circumferential direction. By forming a closed ring, the sensors can be optimally arranged along the entire inner surface of the detector ring.

The representation in step c) can be such that the PET-raw data are displayed to the operator of the PET-scanning device on e.g. a screen in the form of the at least one projection view. The operator can then assess the position of the subject to be scanned based on the displayed projection view(s) and, based on this assessment, re-position the subject to be scanned, if necessary.

In other embodiments, the representation in step c) can alternatively or additionally also be carried out internally, i.e. within the processor of a control unit of the PET-scanning device. In the these embodiments, the at least one projection view is not necessarily displayed on a screen, but can for example be used to automatically assess the position in step d). Edge detection can for example be applied for this purpose. Based on this automatic assessment, the control unit can for example visually or acoustically signal to the operator, that the position of the subject to be scanned needs to be adjusted with respect to the detector. It is also conceivably that the control is adapted to automatically adjust the position of the subject to be scanned relative to the detector based on this automatic assessment.

In yet other embodiments, the assessment in step d) can alternatively or additionally be used for correcting e.g. the acquired raw data or the reconstructed tomographic images, in order to minimize motion artefacts.

Preferably, however, the at least one projection view is displayed on a screen in step d), such that the operator of the system can directly assess the position of the subject to be scanned by means of visual inspection. The screen preferably forms a part of the PET-scanning device. In certain embodiments, however, the screen can also be part of a separate computer station for example, or it can be part of a smart phone or of an external tablet device. In a particularly preferred embodiment, the screen forms a part of the PET-scanning device and is positioned such that it is easily visible by the operator while he repositions the subject to be scanned relative to the detector. For assessing the position of the subject to be scanned relative to the detector, the position of the center of the detector can be displayed on the screen.

The subject to be scanned can for example be a human or animal patient. It can also be plant. The PET-scanning device can be a whole-body scanner having a vertical opening for receiving human patient in a horizontal position. The vertical opening is then sized such, that an adult human patient can be moved therethrough along of his/her longitudinal body axis. In a particularly preferred embodiment, however, the PET-scanning device is a brain-scanner, i.e. a device that is particularly adapted for the PET-imaging of the human brain. In this case, the PET-scanning device preferably comprises a detector ring which is adapted to encompass the head of an adult human patient. The acquisition in step b) then preferably includes the acquisition of PET-raw data of the patient's head. The detector ring can be attached to a main supporting structure in such a way that it can be translationally displaced along e.g. a guide rail of the main supporting structure. The patient can then be in a sitting or lying position during the PET-imaging and the detector can be (fine-) positioned optimally with respect to the patient without having to move the patient.

The method can additionally comprise the steps of:

e) determining based on the assessment of step d), whether the position of the subject to be scanned relative to the detector needs to be adjusted, and f) if it is determined in step e) that an adjustment is necessary, adjusting the position of the subject to be scanned relative to the detector.

Steps e) and/or f) can be carried out by an operator of the PET-scanning device or fully automatically by e.g. a control unit of the PET-scanning device.

For adjusting the position of the subject to be scanned relative to the detector, the subject to be scanned can be moved or the detector can be moved or both. Moving the detector has the advantage that the subject to be scanned has not to be bothered. If the detector is moved, it can particularly be rotated and/or translationally displaced with respect to a main supporting structure of the PET-scanning device. In normal use of the PET-scanning device, the main supporting structure usually carries the main weight, if not the entire weight, of the detector. Thus, the main supporting structure usually serves to support and to hold the detector ring in a stable position during the scanning procedure.

In a preferred embodiment, the method additionally comprises the step of:

g) repeating steps b), c), d), e) and f) until it is determined in step e) that an adjustment is not necessary.

Thus, in accordance to step g), the subject to be scanned is repositioned relative to the detector until the correct position is adopted. While doing so, further PET-raw data are acquired and used, in the form of projection view(s), to assess the position. Using this method, a particularly reliable and fast positioning of the subject to be scanned relative to the detector can be achieved.

Steps b) and c) are preferably carried out in near real time or in real time, in particular within 2 s or less, so that the at least one projection view used to assess the position in step d) reflects the actual position which the subject to be scanned assumes relative to the detector. Steps b) and c) are carried out in near real time, if they are completed within 2 s or less, and in real time, if they are completed within 1 s or less. In certain other embodiments, steps b) and c) can be carried out within e.g. 1 minute or less. A completion of these steps in near real time or in real time has the advantage, that the projection view used to assess the position in step d) reflects the actual position or the subject to be scanned.

The acquisition of the set of PET-raw data in step b) is usually carried out by detecting and integrating positron emissions during a certain time period. The duration of this time period is preferably manually adjustable by an operator of the PET-scanning device. By manually adjusting the duration of this time period, the operator can optimize the data acquisition with regard to quality and time. The time period during which positron emissions are integrated in step b) can preferably be adjusted by the operator over a range of at least 1 s to 1 minute. The duration of the time period is preferably less than one minute, more preferably less than 10 s and even more preferably less than 2 s.

The acquired set of PET-raw data can be stored in the form of a plurality of projection views, the projection views differing from each other with respect to their viewing angles. The stored projection views preferably reflect the complete set of PET-raw data. A storage of the PET-raw data in this way brings about the advantage that e.g. a subset of the stored data can be used directly as the at least one projection view which is used for the assessment in step d).

Thus, the stored data already form the representation of the at least one projection view. The computational time can be minimized in this way.

In other embodiments, it is of course also possible that the PET-raw data are stored in the form of a plurality of sinograms, as it is known to the person skilled in the art, which plurality of sinograms preferably reflect the complete set of PET-raw data. For representing the set of PET-raw data in the form of at least one projection view in step c), the sinograms can then e.g. be reorganized for example by the control unit into a plurality of projection views.

Before step d) the at least one projection view is subjected to an efficiency correction and/or to a geometric normalization correction. This can be achieved by subjecting the acquired set of PET-raw data to an efficiency correction and/or to a geometric normalization correction between steps b) and c) and representing the corrected set of PET-raw data in the form of at least one projection view in step c). Alternatively or additionally, the at least one projection view can be subjected to an efficiency correction and/or to a geometric normalization correction between steps c) and d). The efficiency correction and/or a geometric normalization correction can relate to scanner sensor efficiency correction, in particular to a plane efficiency correction, if cross coincidences between detector sensors on different axial planes are also considered, i.e. in the case of a span greater than 1.

The at least one projection view used to assess the position in step d) is preferably selected from a stored plurality of projection views in response to an input made by an operator of the PET-scanning device. The stored plurality of projection views preferably represents the complete set of PET-raw data. The input made by the operator can particularly relate to the viewing angle of the at least one projection view.

The at least one projection view can be displayed on a touch screen. The input is then preferably entered by the operator via the touch screen. It is for example conceivable that the operator can rotate the displayed projection view on the touch screen, in order to display another view showing a projection from a different viewing angle. The touch screen preferably forms a part of the PET-scanning device and is advantageously attached to a main supporting structure of the PET-scanning device.

The present invention also relates to a PET-scanning device, which is preferably configured to carry out the method indicated above, and which comprises a detector and a control unit, the control unit being configured to acquire, by means of the detector, a set of PET-raw data of a prepositioned subject to be scanned for a series of slices, to represent the acquired set of PET-raw data in the form of at least one projection view, and to display the at least one projection view on a screen of the PET-scanning device, in order to allow an operator of the PET-scanning device to assess the position of the subject to be scanned relative to the detector, and/or to automatically assess the position of the subject to be scanned relative to the detector directly based on the at least one projection view.

The control unit is preferably arranged in a main supporting structure of the PET-scanning device. Advantageously, it is configured to repeatedly acquire, by means of the detector, a set of PET-raw data of a prepositioned subject to be scanned for a series of slices and to represent each of the acquired set of PET-raw data in the form of at least one projection view, in order to be displayed on a screen of the PET-scanning device. In this way, the operator receives, preferably in near real time or in real time, direct information of the position of the inner body part(s) of the subject to be scanned, which are of interest, in relation to the position of the detector.

The control unit preferably has a processor, in particular a digital processor, and a memory in which a computer program is stored, which computer program, when executed by the processor, has the effect that the PET-scanning device, possibly in interaction and, thus, together with an operator, performs the above-mentioned method.

Thus, a computer program, preferably stored on a storage device readable by a computer, is provided, which serves for controlling a PET-scanning device with a detector, in order to position a subject to be scanned in a PET-scanning device, preferably according to the method as indicated, and which is preferably adapted to control a PET-scanning device as indicated. The computer program preferably comprises executable instructions to carry out the method as indicated above, and at least comprises executable instructions to acquire, by means of the detector, a set of PET-raw data of a prepositioned subject to be scanned for a series of slices, to represent the acquired set of PET-raw data in the form of at least one projection view, and to display the at least one projection view on a screen of the PET-scanning device, in order to allow an operator of the PET-scanning device to assess the position of the subject to be scanned relative to the detector, and/or to automatically assess the position of the subject to be scanned relative to the detector directly based on the at least one projection view.

Thus, the computer program carries out central parts of the method described above when executed in a processor of a PET-scanning device or in a processer being connected with a PET-scanning device. The computer program is usually realized as a computer program code element which comprises computer-implemented instructions to cause a processor to carry out a particular method. The computer program can be present in particular in the form of a computer program product on a suitable data carrier, e.g. on a CD-ROM, on a flash memory, etc., or can be provided for download via a network. It can be present in any desired form, e.g. as source code, object code or machine code.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
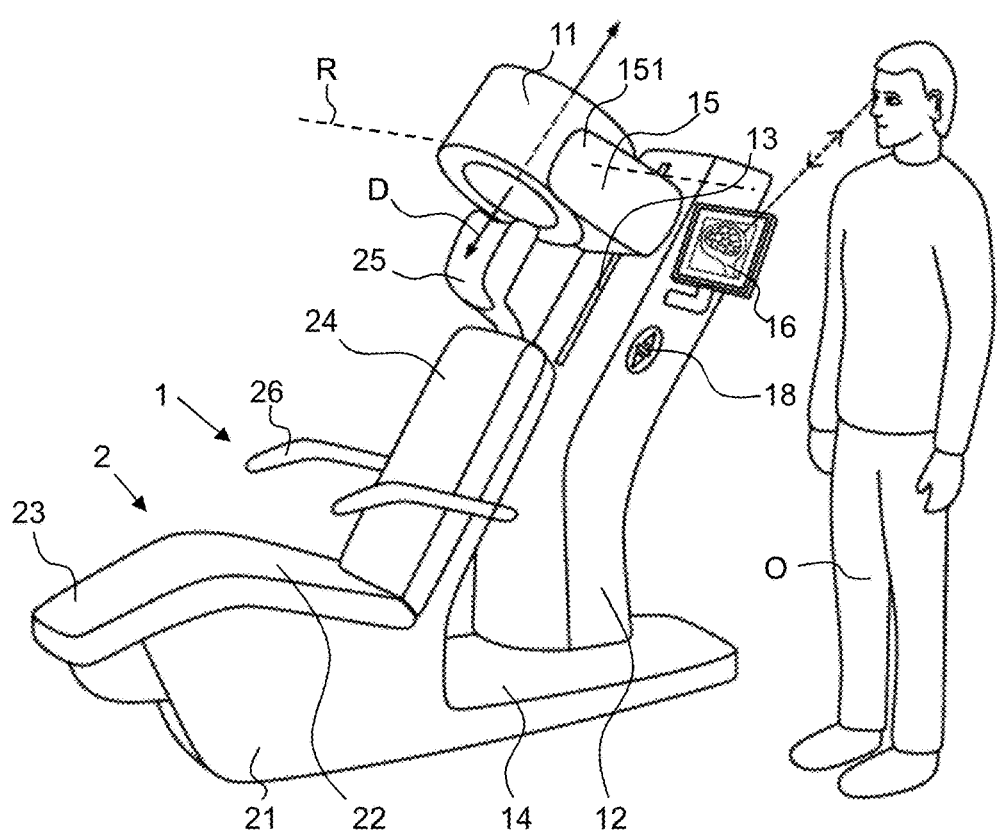
FIG. 1 shows a schematic view of an inventive PET-scanning device according to a first embodiment together with an operator.
Figure 2:
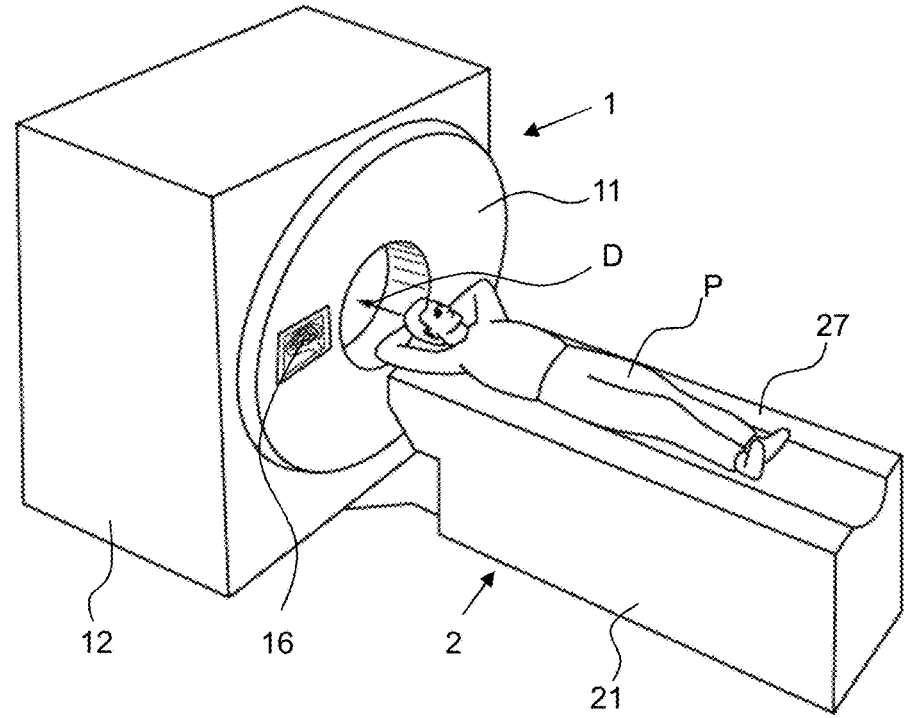
FIG. 2 shows a schematic view of an inventive PET-scanning device according to a second embodiment, with a patient to be scanned.

FIGS. 1 and 2 show two exemplary embodiments of an inventive PET-scanning device 1. The PET-scanning devices 1 as shown in FIGS. 1 and 2 are particularly configured to carry out the inventive method. Elements that have the same or a similar function, but belong to different embodiments, are annotated with the same reference numerals in each case.

In the embodiment as shown in FIG. 1, the PET-scanning device 1 comprises a detector in the form of a detector ring 11, which has a plurality of sensors arranged along of its circular inner surface. The sensors, which are not visible in the figure, serve to detect and measure the PET-radiation emitted in the region of the opening of the detector ring 11

The detector ring 11 is arranged between two holding arms 151 that hold the detector ring 11 between them. The two holding arms 151 form a part of a U-shaped portion 15, which is attached to a main supporting structure 12. The detector ring 11 is rotatable about an axis of rotation R that extends diametrically through the ring and through the two holding arms 151 of the U-shaped portion 15. Furthermore, the detector ring 11 is displaceable together with the U-shaped portion 15 along an inclined direction D relative to the main supporting structure 12. In order to facilitate rotation and displacement of the detector ring 11, one or several handles can be attached to the outer surface of the detector ring 11. It is, however, also possible that the detector ring 11 is displaceable by means of a motor which can be operated by the operator O via a displacement button 18. The displacement button 18 is preferably arranged at the main supporting structure 12, as shown in FIG. 1.

The direction along which the U-shaped portion 15 is displaceable is inclined with respect to the direction of gravity, meaning that it is neither parallel nor perpendicular to the direction of gravity. The U-shaped portion 15 is attached to a guide rail 13 that is provided on the main supporting structure 12 and allows the U-shaped portion 15 to be displaced along the inclined direction D as mentioned. Thus, the guide rail 13 also extends along the inclined direction.

A scanning support 2 is provided for accommodating a human patient in an inclined sitting position during the scanning procedure. Prior to the image acquisition, the patient is accommodated on the scanning support 2 with the detector ring 11 being in the uppermost position of the main supporting structure 12. The detector ring 11 is then displaced and, if necessary, rotated by the operator O into an optimal position for the image acquisition.

The scanning support 2 in the form of a chair-like seating unit comprises a base structure 21 that supports a seat base 22 and a leg support 23 for supporting the legs of the patient during the scanning procedure. Also attached to the base structure 21 is an inclined back support 24. Attached to the back support 24 are pivotable armrests 26 as well as a head support 25. For the image acquisition, the head of the patient rests on the head support 25 and the detector ring 11 is displaced and rotated such that the patient's head is arranged inside of the detector ring 11. Thus, the head support 25 is then likewise arranged inside of the detector ring 11 during the imaging process. In the present embodiment, the scanning support 2 comprises a base structure 14 which form the bottom of the PET-scanning device 1 and connects the scanning support 2 to the main supporting structure 12.

The displacement direction D of the detector ring 11, which is defined by the longitudinal extension of the guide rails 13 that are attached to the main supporting structure 12, approximately corresponds to the longitudinal extensions of the back support 24 and of the head support 25. Thus, the displacement direction D of the detector ring 11 corresponds to the longitudinal main axis of the upper part of the body of the patient, if the patient sits in the scanning support 2 as intended and is ready for the scanning procedure. In order to prevent the patient from moving his head during the image acquisition, a head strap can be used.

For assessing the position of the patient's head relative to the detector ring 11, a screen 16 is preferably attached to the main supporting structure 12. The screen 16 serves to display various information including one or more projection views of the patient's head. Using the screen 16, the operator O can position the patient in such a way, that the part of the body, in particular the part of the brain, of the patient that is to be examined is positioned within the field-of-view of the PET-scanning device 1, that is to say preferably as close to the center of the detector ring 11 as possible.

The screen 16 and/or the displacement button 18 can of course also be arranged distantly of the main supporting structure 12. They can for example be part of a remote computer station that serves to control the PET-scanning device 1 or they can be formed by e.g. a smart phone or an external tablet device. It is, however, usually advantageous if they are arranged such that the operator can operate the displacement button 18 while at the same time inspecting the position of the patient's head on the screen 16.

FIG. 2 shows a second embodiment of an inventive PET-scanning device 1. The PET-scanning device 1 is here in the form of a whole-body scanner with a vertical, stationary detector ring 11. For the imaging, the patient P is accommodated in a lying position on a movable lying surface 27 of the scanning support 2. For positioning the patient P, the lying surface 27 is displaced, together with the patient P, along its longitudinal main direction into the vertical opening of the detector ring 11. Thus, the displacement direction D here coincides with the longitudinal main direction of the patient P, when the patient P is lying as intended on the movably lying surface 27. This can be done manually and/or with motor support. A screen 16, which is here attached to the detector ring 11 and via the detector ring

11 to the main supporting structure 12, serves the operator to see and control the position of the patient P relative to the detector ring 11.

Thus, in the embodiment of FIG. 1, it is the detector ring 11 which is displaced and possibly rotated while the patient remains stationary. In the embodiment of FIG. 2 on the other hand, it is the patient P, i.e. together with the movable lying surface 27, who is moved, in order to be optimally positioned relative to the detector ring 11, which here remains stationary.

Figure 3:
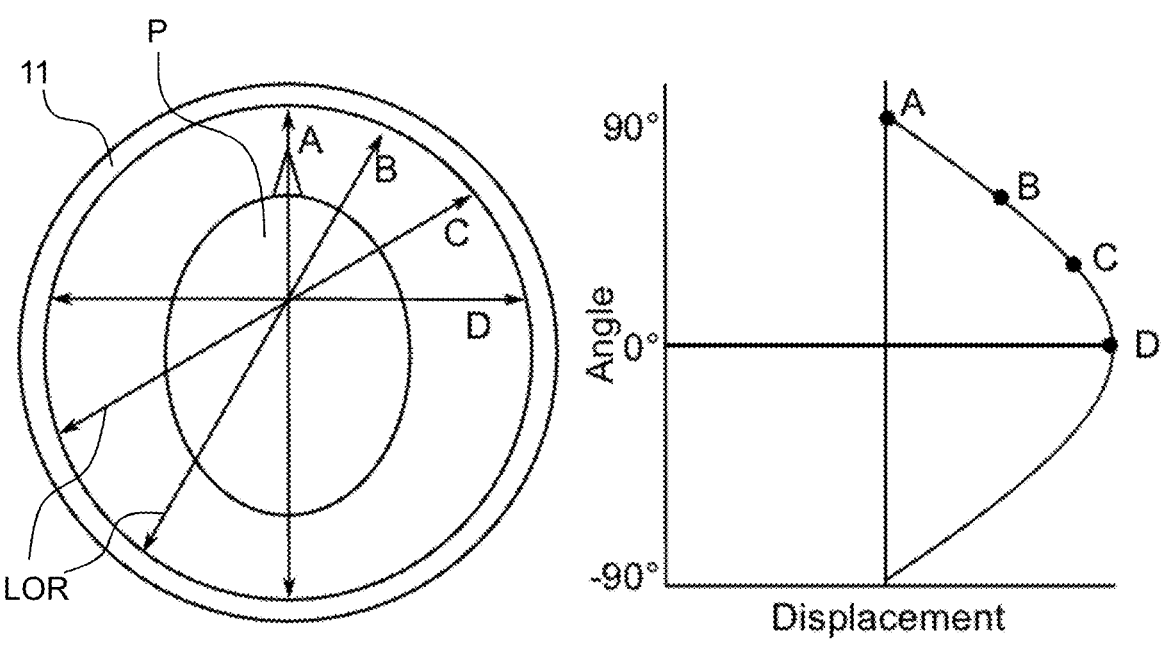
FIG. 3 schematically shows a transversal view of a detector of a PET-scanning device, with the head of a patient being arranged therein, and four exemplary lines of responses being visualized (on the left) as well as a sinogram of the respective cross-sectional plane (on the right)

FIG. 3 shows on the left a transversal view of the head of a patient P that is positioned within the detector ring 11 of an inventive PET-scanning device 1. For the purpose of explanation, four exemplary line of responses LOR are illustrated and annotated with A, B, C and D respectively. The four line of responses LOR relate to emission events that all originate from the same position within the patient's head. The respective emission events are detected by the pair of sensors of the detector ring 11 that are arranged on the two ends of the respective line of response LOR.

On the right side of FIG. 3, a sinogram is shown as it is obtained from the situation on the left side of FIG. 3. In the sinogram, each pair of sensors of the detector ring 11 (and thereby each line of response LOR) corresponds to a particular pixel in the sinogram depending on its orientation angle (y-axis of the sinogram) and distance from the center of the detector ring 11 (x-axis). For each coincidence detection, the line of response LOR for that detection is determined, the pixel in the sinogram associated with that line of response LOR is located, and the value in the pixel is incremented. Thus, each row in the sinogram represents a projection through the scanned object at that angle. By sweeping the angle along the y-axis of the sinogram, a typical half-sinewave type pattern is formed. The person skilled in the art of PET-imaging devices is well acquainted with sinograms.

Sinograms represent a possible way to store the acquired PET-raw data. By storing a sinogram for each slice of acquired data, a complete set of PET-raw data is stored.

Figure 4:
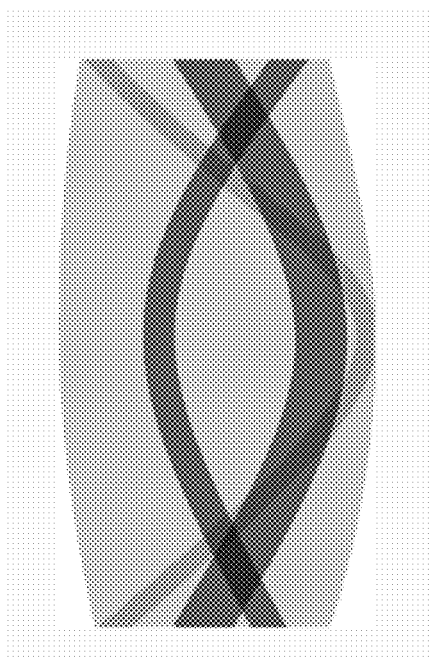
FIG. 4 schematically shows an exemplary sinogram that is formed by a superposition of more than one radiation source (on the left) as well as a typical tomographic image of a patient's brain in transversal view, reconstructed from sinogram data (on the right)
Figure 4:
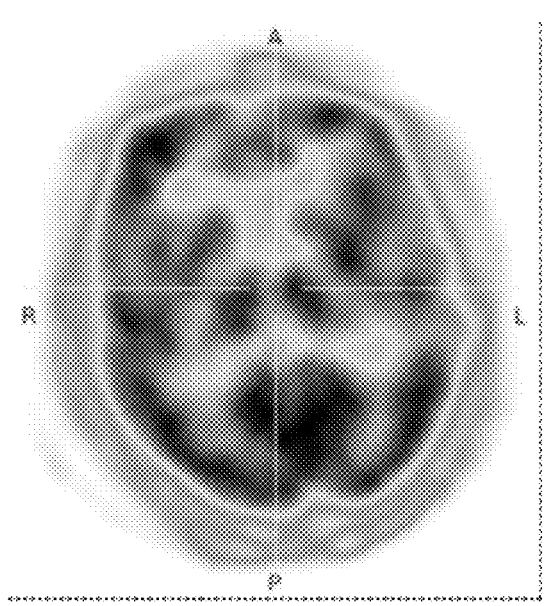

FIG. 4, left side, schematically shows a sinogram resulting from scanning an object that has three distinct regions of increased emission. FIG. 4, right side, shows a reconstructed tomographic brain image as it can be obtained from PET-raw data that are stored in the form of a sinogram. In order the reconstruct the tomographic image from the sinogram, sophisticated processing, e.g. in the form of a forward and back projection method, is usually applied, which requires considerable computational effort and time.

Figure 5:
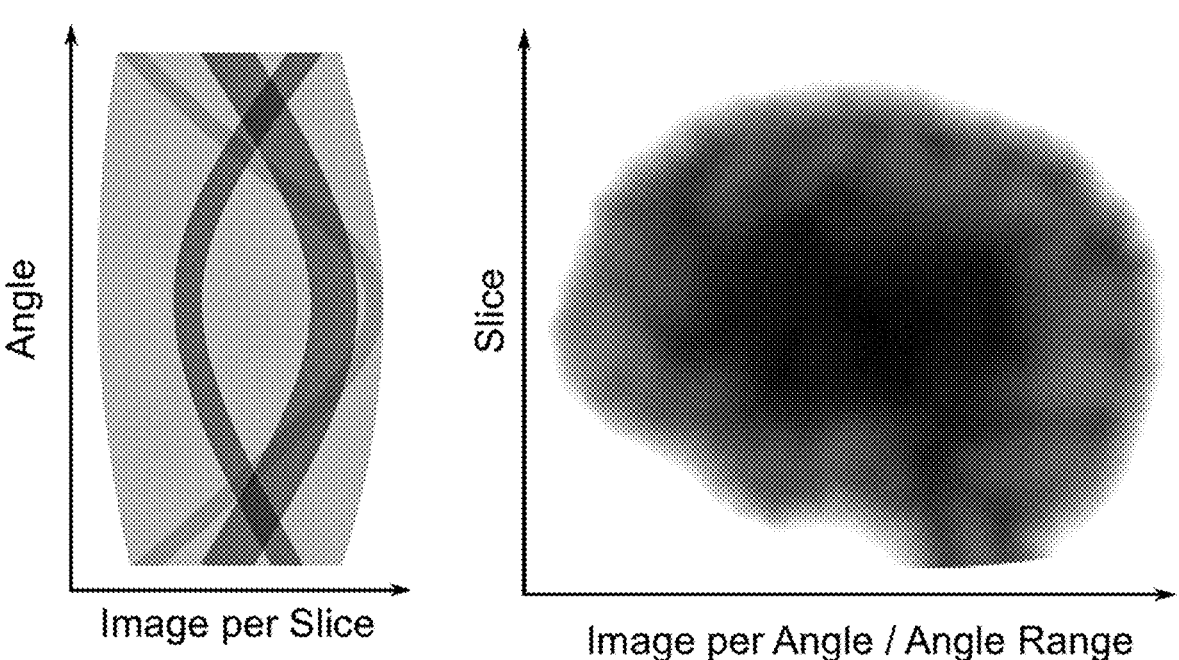
FIG. 5 shows two alternative methods of representing the PET-raw data: Sinogram data (on the left) as well as projection view data (on the right)

FIG. 5 illustrates two alternative methods of representing the acquired set of PET-raw data. On the left side, the same sinogram-representation is shown as in FIG. 4, left side. On the right side, a projection view is shown. The projection view represents, for each pixel, the incremented number of emissions for a certain slice (y-axis of the projection view) and position (x-axis) for a fixed viewing angle. The complete acquired set of PET-raw data can be represented in the form of a plurality of sinograms, with each sinogram corresponding to a different slice, or in the form of a plurality of projection views, with each projection view corresponding to a different viewing angle. Both representations can be displayed immediately, e.g. with a live update, after measuring a line of response. Both representations can also easily be converted into the other representation by means of simply reorganizing the data. No sophisticated and time-consuming processing is required for this purpose.

For assessing the position of the subject to be scanned relative to the detector, a projection view as shown on the right side of FIG. 5 can be used. From this projection view, the operator can easily see the position and orientation of e.g. the brain within the Field-of-View, in order to optimally position (i.e. displace and/or rotate) the detector relative to the patient's head. Since no tomographic reconstruction is required, the projection view can immediately be displayed to the operator after the acquisition of the PET-raw data. In this way, a particularly fast and reliably positioning of the patient can be achieved.

Figure 6:
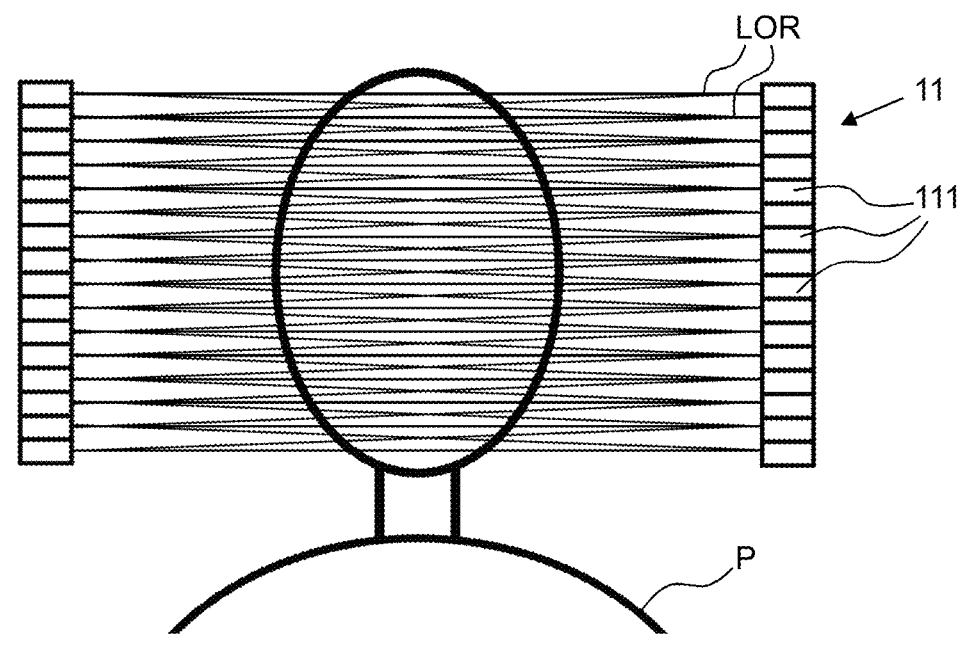
FIG. 6 schematically shows a cross-sectional view of a detector of a PET-scanning device, with the head of a patient being arranged therein, and with an illustration of the coincidences that are detected between detector sensors on different axial planes.

FIG. 6 shows a schematic cross-sectional view through a detector ring 11 having a plurality of sensors 111 arranged along of its circular inner surface. The sensors 111 are arranged on different levels of the detector ring 11 and, thus, form a plurality of sensor rings. Coincidences of emissions that are measured by two oppositely positioned sensors 111 which are each arranged on the same level of the detector ring 11 are referred to as direct coincidences. Thus, detectors of a certain ring are only in coincidence with detectors in the same ring. Direct coincidences are illustrated by means of horizontal line of responses LOR in FIG. 6. For the acquisition of a set of PET-raw data, only direct coincidences can be considered.

To improve the axial sampling and slice sensitivity, detector sensors 111 can be allowed to be in coincidence with sensors 111 in neighbouring rings, referred to as cross coincidences. In FIG. 6, cross coincidences are illustrated by means of oblique line of responses LOR. Combining direct and cross coincidences as e.g. shown in FIG. 6 leads to a greater number of coincidence planes, i.e. 2n−1 planes in the present case, if n is the number of sensor rings. In this context, the term "span" which is well known to the skilled person describes the extent of axial data combined. In the case of FIG. 6, the span is 3.

This concept of combing data of different sensor rings is well known to the skilled person. With the inventive method, it is well possible to apply a span of only 1, i.e. to only consider direct coincidences, in the acquisition of the set of PET-raw data. It is, however, also possible to apply a span greater than 1 for the acquisition, such as e.g. a span of 3, 5, 7 or even greater. If a span of greater than 1 is applied, an efficiency correction is preferably applied with respect to the coincidence planes. As can be seen from FIG. 6, the different coincidence planes can intrinsically have different amount of emission counts. Therefore, an efficiency correction is preferably applied, which can be applied before the PET-raw data are stored or after storing the raw data, but such that the correction is considered in the at least one projection view that is/are shown to the operator O.

Figures 7, 8, 9:
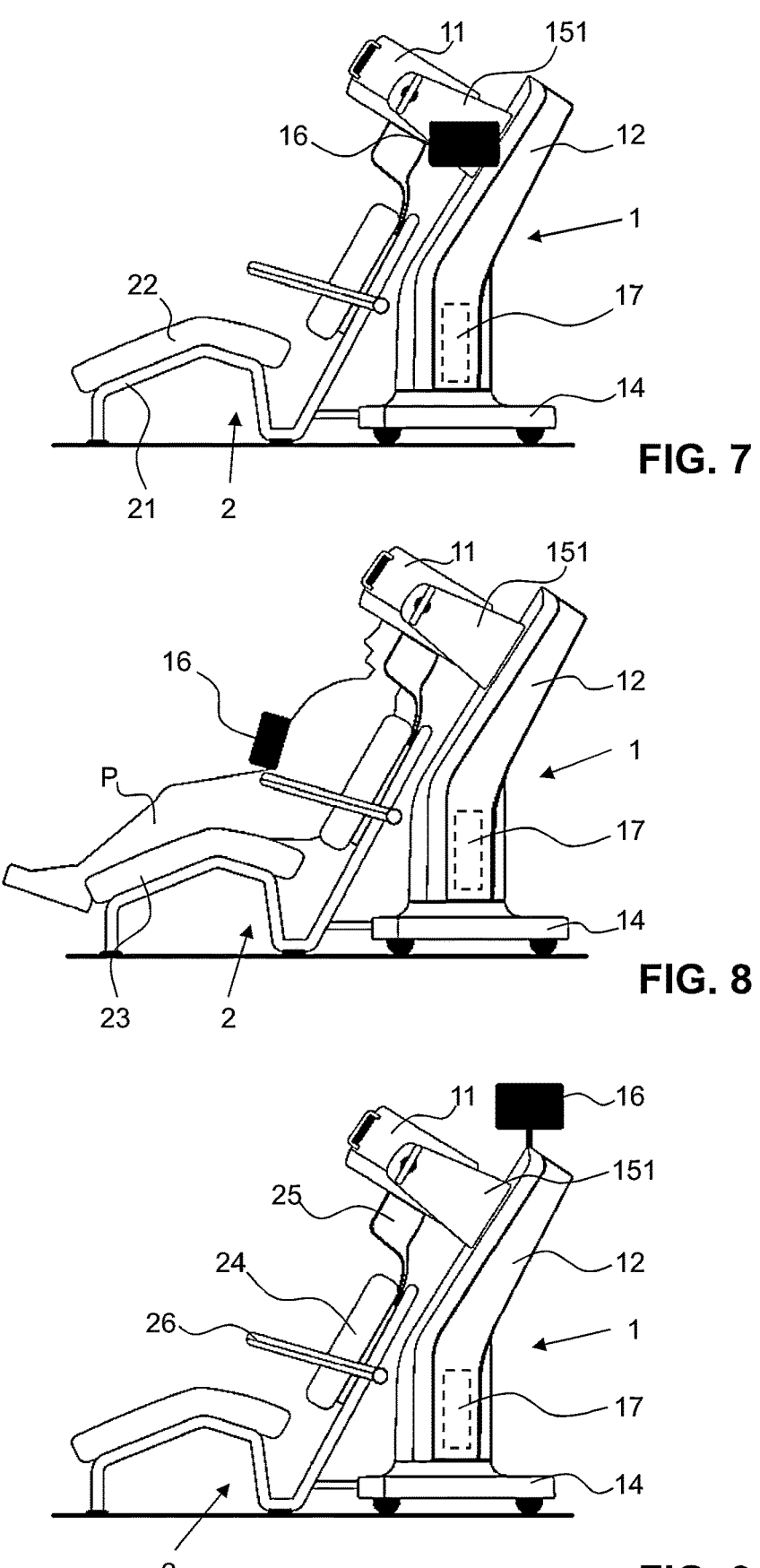
FIG. 7 shows a schematic view of an inventive PET-scanning device according to a first variant of screen position.
FIG. 8 shows a schematic view of an inventive PET-scanning device according to a second variant of screen position.
FIG. 9 shows a schematic view of an inventive PET-scanning device according to a third variant of screen position.

FIGS. 7-9 show three possible variants of how the screen 16 can be positioned. In the variant of FIG. 7, the screen 16 is arranged on one of the holding arms 151, which has the advantage that it is always at the same height as the detector ring 1 and, therefore, well visible to the operator. In particular, the operator can see the region of the patient and the detector ring 11 at the same time as the screen 16 in this case. In the variant of FIG. 8, a screen 16 is provided that is not attached to the main supporting structure 12, but forms a separate part that can be moved freely. Data transmission to and from the screen 16 can e.g. be achieved wirelessly. This variant allows the patient P to see the screen 16 and to himself optimally position his head relative to the detector ring 11. In the variant of FIG. 9, the screen 16 is attached to the upper end of the main supporting structure 12, which has the advantage that it is at eye level of the operator, it the latter is standing in an upright position next to the PET-scanning device 1.

FIGS. 7-9 also show a possible arrangement of a control unit 17 that serves for controlling the PET-scanning device 1. The control unit 17 is here arranged within the main supporting structure 12. Data and/or energy transmission to or from the control unit 17 can be done via one or several cables and/or wirelessly. In other embodiments, the control unit 17 could also be arranged externally. The control unit 17 is preferably connected, by cable or wirelessly, to a user input and output device. The user input and output device can for example be in the form of an external personal computer or it can be a display. It is also possible for the screen 16 to be the input and output device. The screen 16 can particularly be in the form of a touch screen, which preferably allows the operator or the patient to change the viewing angle of the displayed projection view.

Figure 10:
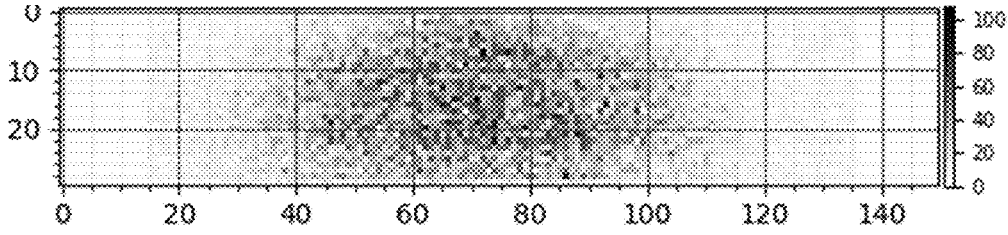
FIG. 10 shows a first exemplary projection view of acquired patient data.
Figure 11:
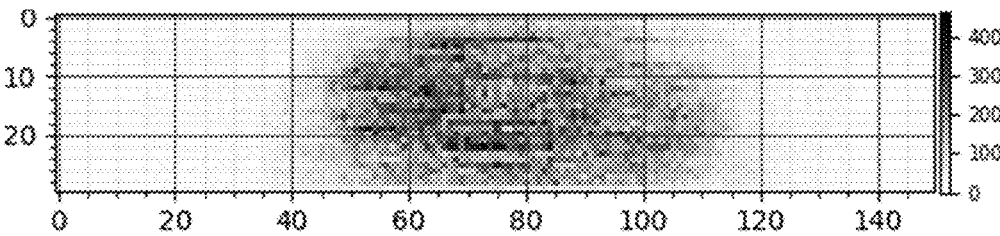
FIG. 11 shows a second exemplary projection view of acquired patient data.

FIGS. 10 and 11 show two exemplary projection views based on data that have been acquired from a patient's head. The projection views have been subjected to an efficiency correction and to a geometric normalization correction in both cases. In the case of FIG. 10, data were acquired during a time period of 10 s. In the case of FIG. 11, the data acquisition took 15 minutes.

The position and orientation of the patient's brain is well recognizable in both FIGS. 10 and 11. From these figures, it can be seen that a projection view based on a reduced data acquisition of 10 s or less can still well be used for assessing the position of the patient relative to the detector. Moreover, the data acquisition duration can be reduced without projection view quality loss by increasing PET-scanning device sensitivity.

Figure 12:
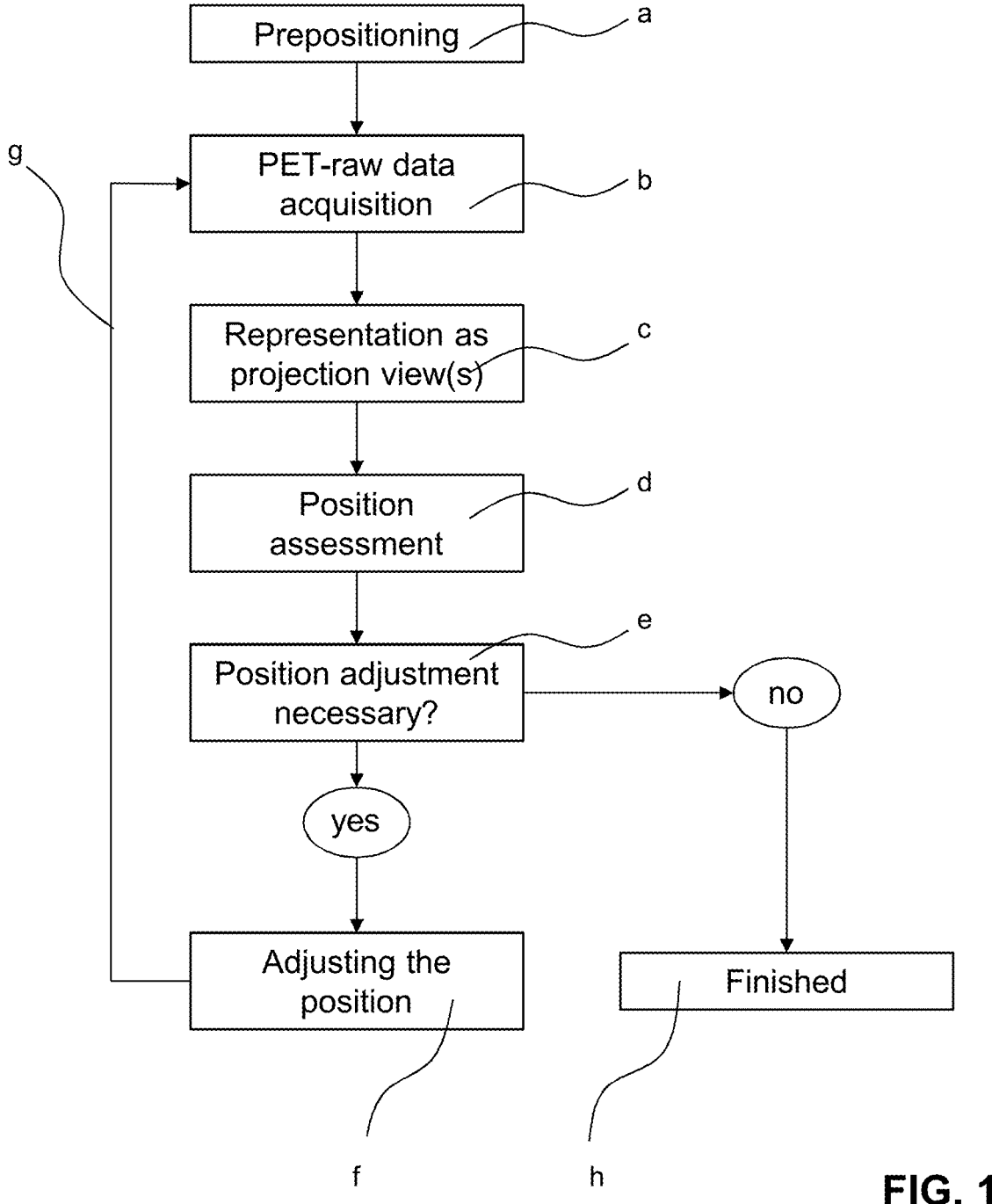
FIG. 12 shows a flow diagram illustrating a preferred embodiment of the inventive method.

FIG. 12 shows a preferred embodiment of the inventive method for positioning a subject to be scanned in a PET-scanning device 1. The method can be applied with any of the PET-scanning devices 1 as shown in FIGS. 1 and 2 as well as in FIGS. 7-9.

In a first step a, the subject to be scanned, e.g. the patient P, is prepositioned in the PET-scanning device 1 and a positioning mode of the PET-scanning device 1 is activated. In the positioning mode, PET-raw data are acquired, in order to generate at least one projection view. Usually, in the positioning mode, the acquired raw data are not reconstructed and not saved for later use, e.g. preferably no list mode data are saved. The raw data acquired in the positioning mode typically only serve for correctly positioning the patient. For this purpose, the at least one projection view is advantageously continuously updated during the positioning. In the positioning mode, steps b-g are preferably carried out as follows:

A first set of PET-raw data is acquired in step b. The acquired set of PET-raw data is represented in the form of at least one projection view in step c, which means that e.g. a subset of the PET-raw data can be selected, it the data are already stored in the form of projection views, or that e.g. the PET-raw data are reorganized into projection views of which a subset is then selected, if the data are stored in the form of sinograms.

In step d, the position of the subject to be scanned is assessed relative to the detector based on the at least one projection view. This can be done by an operator based on one or more projection views that are displayed on a screen or automatically by the control unit. The position assessment as carried out by the operator can particularly involve the determination, whether the part of the patient's body which is of interest, such as e.g. the patient's brain, is within the Field-of-View of the PET-scanning device. For automatically assessing the patient's position, the detector count rate and/or the detector sensitivity can for example be considered, e.g. by visualizing the detector count rate and/or the detector sensitivity on the screen or by comparing the projection view(s) automatically with the detector count rate and/or the detector sensitivity.

In the next step e, it is determined, based on the position assessment of step d, whether the position of the subject to be scanned relative to the detector needs to be adjusted.

If the answer in step e is "no", the subject to be scanned is correctly positioned relative to the detector, which means that the positioning of the subject to be scanned is completed (step h). The positioning mode of the PET-scanning device 1 can then be terminated and the acquisition of the higher quality PET-data, which are of actual interest, can be started. The acquired higher quality PET-data are usually reconstructed and saved, in order to medically assess the obtained reconstructed tomographic images of the part of the patient's body which is of interest.

If the answer in step e is "yes", the position of the subject to be scanned relative to the detector is adjusted, either manually by the operator or automatically by the control unit. For this purpose, the subject to be scanned and/or the detector can be moved accordingly. After or already during the position adjustment, steps a-e and, if necessary, f are repeated (g) until the answer in step e is "no" and the procedure can be finished (step h).

The present invention is of course not limited on the embodiments as described and as shown in FIGS. 1 to 12. The elements presented and described with respect to FIGS. 1 to 12 can of course be exchanged and combined and many modifications are possible. Features that have been indicated with respect to certain embodiments only, can well be provided in other embodiments, too. For example, in the embodiment of FIG. 2, the screen 16 can well for a separate and movable part, as in the embodiment of FIG. 8. The method does not necessarily need the step of adjusting the subject to be scanned. In particular, if it turns out that the patient has already been optimally positioned in the prepositioning step, an adjustment of his position is not necessary anymore. If the prepositioning is almost, but not perfectly optimal, the position of the patient can also remain unadjusted and the already acquired raw data or the raw data that are acquired in the following can be corrected based on the position assessment. A plurality of further modifications is possible.

The invention claimed is:

1. A method to position a subject to be scanned in a positron emission tomography (PET)-scanning device, comprising the steps of:
   a) prepositioning the subject to be scanned in the PET-scanning device;
   b) acquiring, by means of a detector of the PET-scanning device, a set of PET-raw data of the subject to be scanned for a series of slices;
   c) representing the acquired set of PET-raw data in the form of at least one projection view; and
   d) assessing the position of the subject to be scanned relative to the detector directly based on the at least one projection view.

2. The method according to claim 1, wherein the at least one projection view is displayed on a screen in step d).

3. The method according to claim 2, wherein the screen forms a part of the PET-scanning device.

4. The method as claimed in claim 1, additionally comprising the steps of:
   e) determining based on this assessment, whether the position of the subject to be scanned relative to the detector needs to be adjusted, and f) if it is determined in step e) that an adjustment is necessary, adjusting the position of the subject to be scanned relative to the detector.

5. The method according to claim 4, wherein for adjusting the position of the subject to be scanned relative to the detector in step f), the detector is rotated and/or translationally displaced with respect to a main supporting structure of the PET-scanning device.

6. The method as claimed in claim 4, additionally comprising the step of:
   g) repeating steps b), c), d), e) and f) until it is determined in step e) that an adjustment is not necessary.

7. The method as claimed in claim 6, wherein steps b) and c) are carried out in near real time or in real time, so that the at least one projection view used to assess the position in step d) reflects the actual position which the subject to be scanned assumes relative to the detector.

8. The method as claimed in claim 7, wherein steps b) and c) are carried out within 2 s or less.

9. The method as claimed in claim 1, wherein the acquired set of PET-raw data is stored in the form of a plurality of projection views, the projection views differing from each other with respect to their viewing angles.

10. The method as claimed in claim 9, wherein the stored projection views reflect the complete set of PET-raw data.

11. The method as claimed in claim 1, wherein the acquisition of the set of PET-raw data in step b) is carried out by detecting and integrating positron emissions during a certain time period, and wherein the duration of this time period is manually adjusted by an operator of the PET-scanning device.

12. The method as claimed in claim 1, wherein the acquisition of the set of PET-raw data in step b) is carried out by detecting and integrating positron emissions during a certain time period, and wherein the duration of this time period is less than one minute.

13. The method as claimed in claim 12, wherein the duration of the time period is less than 10 s.

14. The method as claimed in claim 13, wherein the duration of the time period is less than 2 s.

15. The method as claimed in claim 1, wherein, before step d), the at least one projection view is subjected to an efficiency correction and/or to a geometric normalization correction.

16. The method as claimed in claim 1, wherein the at least one projection view used to assess the position in step d) is selected from a stored plurality of projection views in response to an input made by an operator of the PET-scanning device.

17. The method as claimed in claim 16, wherein the at least one projection view is displayed on a touch screen, and wherein the input is entered by the operator via the touch screen.

18. The method as claimed in claim 1, wherein the subject to be scanned is a human patient, and wherein the acquisition in step b) includes the acquisition of PET-raw data of the patient's brain.

19. A PET-scanning device, which comprises a detector and a control unit, the control unit being configured
   to acquire, by means of the detector, a set of PET-raw data of a prepositioned subject to be scanned for a series of slices,
   to represent the acquired set of PET-raw data in the form of at least one projection view, and
   to display the at least one projection view on a screen of the PET-scanning device, in order to allow an operator of the PET-scanning device to assess the position of the subject to be scanned relative to the detector, and/or to automatically assess the position of the subject to be scanned relative to the detector directly based on the at least one projection view.

20. A non-transitory computer readable medium comprising a computer program for controlling a PET-scanning device with a detector, wherein the computer program comprises executable instructions:

to acquire, by means of the detector, a set of PET-raw data of a prepositioned subject to be scanned for a series of slices, to represent the acquired set of PET-raw data in the form of at least one projection view, and to display the at least one projection view on a screen of the PET-scanning device, in order to allow an operator of the PET-scanning device to assess the position of the subject to be scanned relative to the detector, and/or to automatically assess the position of the subject to be scanned relative to the detector directly based on the at least one projection view.

* * * * *